United States Patent
Yoo et al.

(10) Patent No.: US 12,222,997 B2
(45) Date of Patent: Feb. 11, 2025

(54) ASSOCIATED QUERY DISPLAY SYSTEM OF CLINICAL TRIAL CASE REPORT SYSTEM AND THE METHOD

(71) Applicant: JNPMEDI INC., Incheon (KR)

(72) Inventors: Hui Dong Yoo, Incheon (KR); Young Yong Park, Incheon (KR)

(73) Assignee: JNPMEDI INC., Incheon (KR)

( * ) Notice: Subject to any disclaimer, the term of this patent is extended or adjusted under 35 U.S.C. 154(b) by 283 days.

(21) Appl. No.: 17/838,824

(22) Filed: Jun. 13, 2022

(65) Prior Publication Data

US 2023/0028951 A1 Jan. 26, 2023

(30) Foreign Application Priority Data

Jul. 26, 2021 (KR) .................. 10-2021-0097526

(51) Int. Cl.
*G06F 16/9535* (2019.01)
*G06F 16/9532* (2019.01)
*G06F 16/9538* (2019.01)
*G06F 16/954* (2019.01)

(52) U.S. Cl.
CPC ...... *G06F 16/9532* (2019.01); *G06F 16/9535* (2019.01); *G06F 16/9538* (2019.01); *G06F 16/954* (2019.01)

(58) Field of Classification Search
CPC .. G06F 16/951; G06F 16/953; G06F 16/9532; G06F 16/9535; G06F 16/9536; G06F 16/9538; G06F 16/954
See application file for complete search history.

(56) References Cited

U.S. PATENT DOCUMENTS

| | | | | |
|---|---|---|---|---|
| 6,108,635 | A * | 8/2000 | Herren | G16H 10/60 600/300 |
| 2011/0314026 | A1* | 12/2011 | Pickens | G06F 16/33 707/E17.014 |
| 2014/0222463 | A1 | 8/2014 | Guthrie, Jr. et al. | |
| 2017/0076046 | A1* | 3/2017 | Barnes | G06F 16/951 |
| 2019/0228095 | A1* | 7/2019 | Ergun | G06F 16/2455 |
| 2021/0248150 | A1* | 8/2021 | Stockton | G16H 10/20 |
| 2021/0391075 | A1* | 12/2021 | Marks | G16H 10/60 |

FOREIGN PATENT DOCUMENTS

KR 10-2006-0122552 A 11/2006
KR 10-2021-0015338 A 2/2021

* cited by examiner

*Primary Examiner* — Kris E Mackes
(74) *Attorney, Agent, or Firm* — Bridgeway IP Law Group, PLLC; Sang Ho Lee; Hyun Woo Shin (57) ABSTRACT

Provided is an associated query display system and a method thereof, and an associated query display method according to an embodiment includes the steps of: storing a query generation condition received from a manager terminal; receiving clinical trial data from a user terminal; determining whether the clinical trial data corresponds to the query generation condition; storing a query cause item that causes generation of a query; and outputting the query on the user terminal, and providing an associated query display function capable of tracking and accessing the query cause item.

11 Claims, 6 Drawing Sheets

| | > [Visit 1] Demographic information survey: SEX(SEX) (1) | | |
|---|---|---|---|
| | > [Visit 1] Pregnancy Test: Pregnancy(PTYNC) (1) ──BT2 | | |
| [Status] The status is 'Withdrawn' When the pregnancy test result is confirmed as positive', but the pregnancy status is confirmed as 'No' system | | 🔗 | ☑ |
| Reason for screen failure | ○ Inappropriate Inclusion/Exclusion criteria<br>○ Withdraw consent<br>○ Etc<br>　Please enter the reason for screening failed | | ◇ 💬 📋 📄 |

ASSOCIATED QUERY DISPLAY SYSTEM OF CLINICAL TRIAL CASE REPORT SYSTEM AND THE METHOD

CROSS-REFERENCE TO RELATED APPLICATION(S)

The instant application claims priority to Korean patent application number 10-2021-0097526 filed no Jul. 26, 2021, the entire contents of which is hereby incorporated by reference.

BACKGROUND OF THE INVENTION

Field of the Invention

The present invention relates to a system and method for displaying an associated query of a clinical trial electronic case report system, and proposes a system and method for providing a service for tracking and accessing a query generated when clinical trial data is input or collected.

Background of the Related Art

As interest in health increases in modern society, the number of clinical trials conducted for development of new medicines is increasing rapidly. Many studies are conducted recently to digitize Case Report Forms (CRFs) used for conducting clinical trials and derive reliable clinical trial results.

Particularly, a monitor agent, a data manager, or the like issues, in the process of collecting clinical trial data, a query requesting those who have input the clinical trial data to confirm input data to enhance reliability of the clinical trial data.

SUMMARY OF THE INVENTION

An object of the present invention is to provide an associated query display system and a method thereof, which can facilitate query management on clinical trial data, and move, when a query is generated, to an item that causes the query on a page where the query is output.

The technical problems of the present invention are not limited to the technical problems mentioned above, and other unmentioned technical problems will be clearly understood by those skilled in the art from the following description.

To accomplish the above object, according to an aspect of the present invention, there is provided an associated query display method comprising the steps of: storing a query generation condition received from a manager terminal; receiving clinical trial data from a user terminal; determining whether the clinical trial data corresponds to the query generation condition; storing a query cause item that causes generation of a query; and outputting the query on the user terminal, and providing an associated query display function capable of tracking and accessing the query cause item.

The step of storing a query generation condition received from a manager terminal may include the step of receiving and storing the query generation condition and a message to be output in correspondence to the query generation condition from the manager terminal.

The associated query display function may be provided as a user interface (UI) including page information including the query cause item and a link for moving to a page address including the query cause item.

The associated query display method may further comprise the step of providing, when the user terminal moves to a page including the query cause item through the associated query display function, a cause item display function for highlighting the query cause item on the moved page.

The associated query display method may further comprise the step of providing a function of directly moving from the moved page to a page including a query target item, which is a target of query generation.

The associated query display method may further comprise the step of providing a query cause item list to the manager terminal and/or the user terminal.

The query cause item list may include the query cause item stored at the step of storing a query cause item that causes generation of a query, and query generation related information including a time and date when the query is generated.

To accomplish the above objects, according to another aspect of the present invention, there is provided an associated query display system comprising: a query condition setting unit for receiving a query generation condition from a manager terminal; a query generation determination unit for determining whether clinical trial data input from a user terminal corresponds to the received query generation condition; a query item storage unit for storing a query cause item that causes generation of a query; and a query output unit for outputting the query on the user terminal, and providing an associated query display function capable of tracking and accessing the query cause item.

The associated query display function may be provided as a user interface (UI) including page information including the query cause item and a link for moving to a page address including the query cause item.

The query output unit may provide, when the user terminal moves to a page including the query cause item through the associated query display function, a cause item display function for highlighting the query cause item on the moved page.

The query output unit may provide a function of directly moving from the moved page to a page including a query target item, which is a target of query generation.

The query item storage unit may provide a query cause item list including the query cause item and query generation related information including a time and date when the query is generated.

Details of other embodiments are included in the detailed description and drawings.

DETAILED DESCRIPTION OF THE PREFERRED EMBODIMENT

Hereinafter, preferred embodiments of the present invention will be described in detail with reference to the accompanying drawings in order to clarify the technical spirit of the present invention. In describing the present invention, when it is determined that a detailed description of a related well-known function or component may unnecessarily obscure the subject matters of the present invention, the detailed description thereof will be omitted. Elements having substantially the same functional configuration among the drawings are given the same reference numbers and reference symbols as much as possible even though they are shown in different drawings. For convenience of explanation, the device and method will be described together if necessary.

Hereinafter, the term "unit" is defined herein as having its broadest definition to ordinary skill in the art to refer to software including instructions executable in a non-transitory computer-readable medium that would perform the associated function when executed, a circuit or a processor designed to perform the associated function, hardware designed to perform the associated function, or a combination of them.

Figure 1:
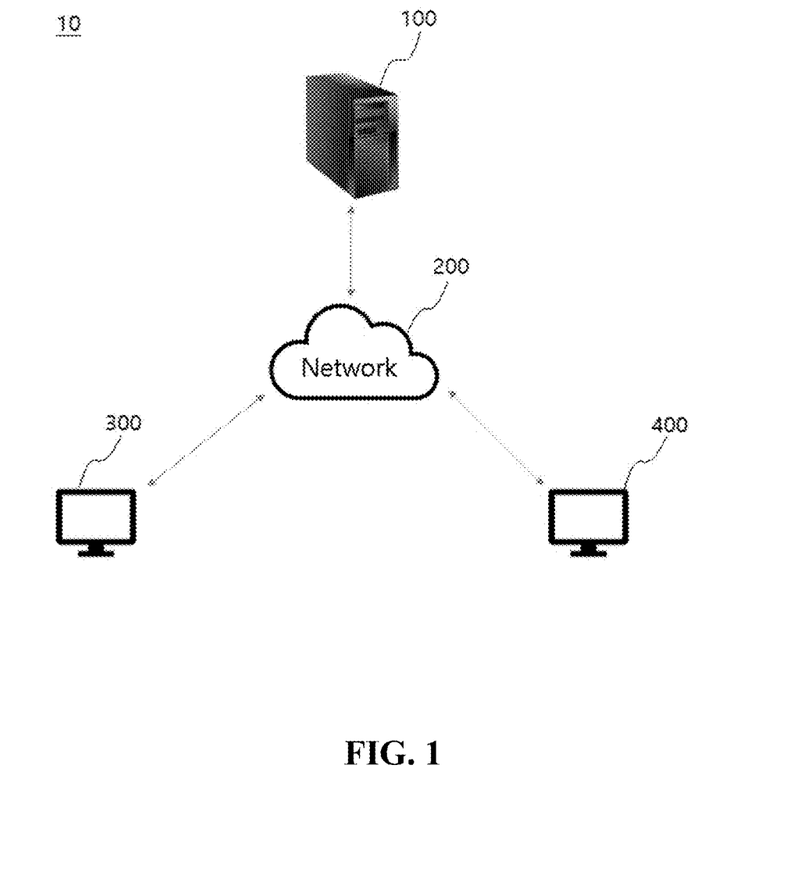
FIG. 1 is a schematic diagram showing an associated query display system according to an embodiment.

FIG. 1 is a schematic diagram showing an associated query display system according to an embodiment.

Referring to FIG. 1, an associated query display system 10 according to an embodiment may include a platform 100, at least one manager terminal 300, and at least one user terminal 400.

The platform 100 may collect clinical trial data, and provide an associated query display function when a query is generated while the clinical trial data is collected. A query may mean a message requesting confirmation of input data, and the associated query display function may mean a function capable of tracking and accessing a cause item of a generated query.

Although it is described below focusing on that the platform 100 provides a function of collecting clinical trial data and displaying an associated query on one manager terminal 300 and one user terminal 400 for convenience of explanation, it is not limited thereto. For example, the platform 100 may provide a function of collecting clinical trial data and displaying an associated query on one manager terminal 300 and a plurality of user terminals 400, or provide a function of collecting clinical trial data and displaying an associated query on a plurality of manager terminals 300 and a plurality of user terminals 400. In addition, the platform 100 may provide a function of collecting clinical trial data and displaying an associated query on a plurality of manager terminals 300 and one user terminal 400.

The platform 100 is provided as a computerized system, and may provide a function of collecting clinical trial data and displaying an associated query through any one among, for example, an application program, an application, and a website.

The platform 100 may provide a stored electronic case report form to the manager terminal 300, and receive and store a query generation condition from the manager terminal 300. The platform 100 may provide a stored electronic case report form to the user terminal 400, and receive clinical trial data from the user terminal 400. Although the electronic case report form may be received and stored from the manager terminal 300, it is not limited thereto.

In addition, the platform 100 may output a query on the user terminal 400 according to a query generation condition stored in the process of receiving the clinical trial data from the user terminal 400, and provide an associated query display function. Accordingly, it may be advantageous for the user terminal 400 to reduce the time and cost required for managing the clinical trial data as it is easy to manage a query generated when the clinical trial data is collected, and the user terminal 400 may easily track and access a query cause item when a query is generated.

Furthermore, the associated query display system according to an embodiment may increase reliability of the clinical trial data by securing consistency of the clinical trial data. A detailed description of the platform 100 will be described below with reference to FIG. 2.

The manager terminal 300 and the user terminal 400 may be devices capable of accessing the platform 100 through a wired/wireless communication network such as the Internet and/or an intranet. For example, the manager terminal 300 and the user terminal 400 may be a mobile terminal such as a laptop computer, a handheld device, a smart phone, a tablet PC or the like, a desktop computer, or a device using such a device or directly or indirectly connected thereto.

The manager using the manager terminal 300 and the user using the user terminal 400 may access at least any one among an application program, an application, and a website provided by the platform 100 through their own terminals, and may be provided with an associated query display function from the platform 100.

The manager terminal 300 may be a terminal of any one among an institution, a corporation, a company, and an individual that manages clinical trial data. For example, the manager terminal 300 may be a terminal of a data manager (DM) who manages and supports information on the overall progress of clinical trial. As another example, although the manager terminal 300 may be a terminal of any one among a clinical trial director, a clinical trial project manager (PM), and a clinical research associate (CRA), it is not limited thereto.

The user terminal 400 may be a terminal of any one among an institution, a corporation, a company, and an individual related to clinical trial. For example, although the user terminal 400 may be a terminal of any one among a clinical research coordinator (CRC), a study coordinator (SC), and a research nurse who conducts a clinical trial and inputs clinical trial data, it is not limited thereto, and the user terminal 400 may include a terminal of a person related to a corresponding clinical trial, such as a clinical trial director, a clinical trial project manager, or the like.

The network 200 is a communication network through which the platform 100, the manager terminal 300, and the user terminal 400 communicate with each other, and may be configured without regard to a particular communication form. For example, although the network 200 may be configured of various communication networks such as a Personal Area Network (PAN), a Local Area Network (LAN), a Metropolitan Area Network (MAN), and a Wide Area Network (WAN), it is not limited thereto.

Figure 2:
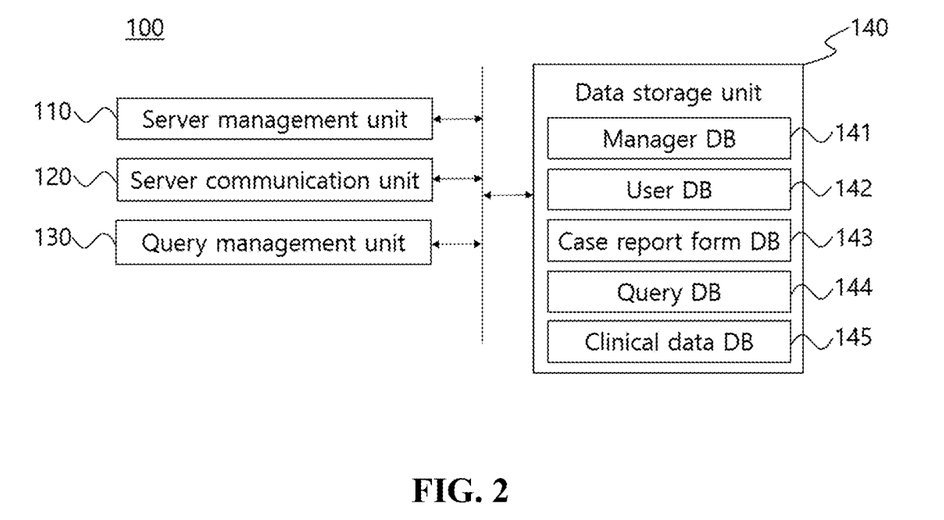
FIG. 2 is a block diagram schematically showing the configuration of a platform according to an embodiment.

FIG. 2 is a block diagram schematically showing the configuration of a platform according to an embodiment.

Referring to FIG. 2, the platform 100 may include a server management unit 110, a server communication unit 120, a query management unit 130, and a data storage unit 140.

In order to provide a function of receiving a query generation condition or displaying an associated query on the manager terminal 300 and the user terminal 400, the server management unit 110 may request personal information such as an e-mail, an ID, a password, a phone number, and the like and/or information on a company, a corporation or an organization (hereinafter, referred to as manager information or user information) and store the information in the data storage unit 140.

The server management unit 110 may receive an electronic case report form and electronic case report form related information from the manager terminal 300 through the server communication unit 120, and store them in the data storage unit 140. In this specification, the electronic case report form related information may include a clinical trial title, a protocol number, manager information, user information, and the like related to a corresponding electronic case report form. When a plurality of managers uses the platform 100, the server management unit 110 may classify the electronic case report form according to the manager information stored as the electronic case report form related information and store the classified electronic case report form in the data storage unit 140.

The server management unit 110 may provide the electronic case report form to the user terminal 400 in response to a request of the user terminal 400. For example, the server management unit 110 may provide the electronic case report form to the user terminal 400 through any one among an application program, an application, and a website. When a plurality of users uses the platform 100, the server management unit 110 may provide each user terminal 400 with an electronic case report form corresponding to user information stored as the electronic case report form related information.

The server communication unit 120 may perform data communication with the manager terminal 300 and the user terminal 400 in a wired or wireless manner through the network 200. The server communication unit 120 may transmit and receive data between the platform 100, the manager terminal 300, and the user terminal 400 through a wired Internet communication method that supports Transmission Control Protocol/Internet Protocol (TCP/IP), or the like, or at least any one among various wireless communication methods such as Wideband Code Division Multiple Access (WCMDA), Long Term Evolution (LTE), Wireless Broadband Internet (WiBro), Wi-Fi (Wireless Fidelity), and the like.

The query management unit 130 may receive a query generation condition and a message to be output when a query is generated from the manager terminal 300, and store them in the data storage unit 140. In addition, when data is input by the user terminal 400, the query management unit 130 outputs a query according to the stored query generation condition, stores the items included as the query generation condition of the output query, and provide an associated query display function to the manager terminal 300 and/or the user terminal 400.

Figure 3:
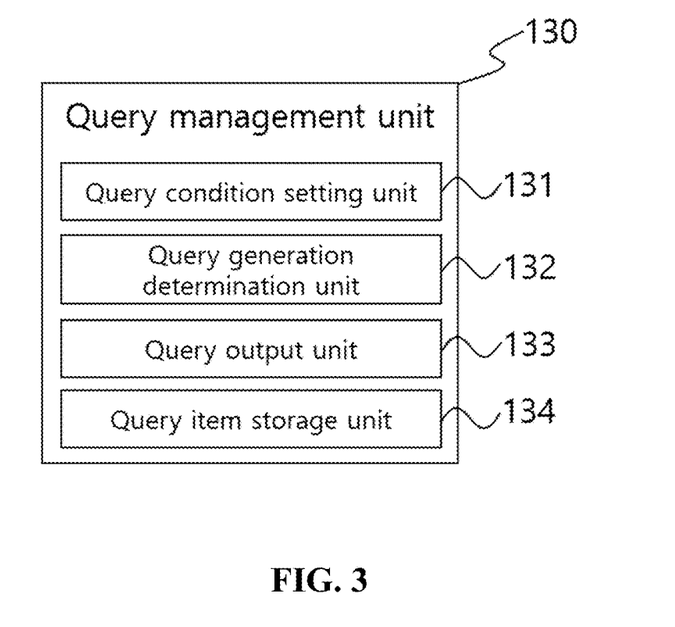
FIG. 3 is a block diagram schematically showing the configuration of a query management unit according to an exemplary embodiment.

FIG. 3 is a block diagram schematically showing the configuration of a query management unit according to an exemplary embodiment.

Referring to FIG. 3, the query management unit 130 may include a query condition setting unit 131, a query generation determination unit 132, a query output unit 133, and a query item storage unit 134.

The query condition setting unit 131 may receive a query generation condition and a message to be output when a query is generated, which are transmitted from the manager terminal 300 through the server communication unit 120. The query generation condition may be set in correspondence to each electronic case report form. However, it is not limited thereto, and for example, the query generation condition may be commonly set for a plurality of electronic case report forms.

Although the query condition setting unit 131 may request electronic case report form related information of an electronic case report form, for which a query generation condition is to be set, in order to receive the query generation condition from the manager terminal 300, it is not limited thereto.

The query generation condition is that a clinical trial data input by the user terminal 400 includes at least one among an input error and a logic error, and may mean a condition set by the manager terminal 300.

Specifically, the input error of the clinical trial data may include a case including an error in the input data format and a case including an error in the input data content. However, it is not limited thereto. For example, the input error of the clinical trial data may include a case in which data input is omitted.

Examples of an error in the input data format include a case of inputting characters in an item that requires a numeric input, a case of inputting a number in an item that requires a character input, a case of dissatisfying the condition of the maximum or minimum length of characters (or number), and the like. In addition, examples of an error in the input data content include a case of inputting a test subject's visit date as a date later than the data input date, a case of checking the written consent as 'No', and a case of inputting a data out of a preset numerical range, and the like. However, the embodiments are not limited thereto, and various examples related to input error of clinical trial data known in the art may be included.

The logic error of clinical trial data may include a case where there is a logic error between at least one among a plurality of previously input data and a currently input data. That is, the query generation condition of any one item may be set based on a relationship with another item, or may be set based on a relationship with a plurality of items.

As an example of setting a query generation condition for any one item based on a relationship with another item, a query generation condition of progressing a test subject's visit after written consent is obtained may be set. That is, a case in which the date input in the item of the first visit date is input as a date older than the date input in the item of the date of written consent may be set as the query generation condition.

In addition, as an example of setting a query generation condition of any one item based on a relationship with a plurality of items, a query generation condition of an item of 'Confirmed positive pregnancy test result' among the clinical trial withdrawn items may be set based on a relationship with an item of gender and an item of pregnancy. That is, although the 'Confirmed positive pregnancy test result' is selected among the clinical trial withdrawn items, a case of selecting sex as 'male' or pregnancy as 'no' as previous input data may be set as a query generation condition.

Hereinafter, a query generation condition of an item of 'Confirmed positive pregnancy test result' among the clinical trial withdrawn items will be mainly described as an example of a query generation condition for convenience of explanation. However, the query generation condition may include various examples of query generation conditions for inputting clinical trial data known in the art, within the scope of sharing the technical spirit.

The query condition setting unit 131 may store the query generation condition and a message to be output when a query is generated, which are received from the manager terminal 300, in the data storage unit 140. In this case, the query condition setting unit 131 may store the message to be output when a query is generated in the data storage unit 140 in correspondence to each query generation condition.

The query generation determination unit 132 may determine whether data input from the user terminal 400 corresponds to a previously stored query generation condition. When data for each item of the electronic case report form is input from the user terminal 400, the query generation determination unit 132 may confirm the query generation condition set for each item, and determine whether the data input from the user terminal 400 corresponds to the query generation condition.

When the data input into the query target item corresponds to the query generation condition, the query generation determination unit 132 may request the query output unit 133 to output a query, and store an item that causes generation of the query (hereinafter, referred to as a query cause item) in the query item storage unit 134.

The query output unit 133 may output a query on the user terminal 400 in response to a request of the query generation determination unit 132. The query output unit 133 may output a message, which is stored in the data storage unit 140 in correspondence to a query generation condition and to be output when a query is generated, as a query. The query output unit 133 may output the query on the user terminal 400 through any one among an application program, an application, and a website. In this case, the query output unit 133 may output the query on the page where the query target item is displayed.

When a query is output, the query output unit 133 may provide an associated query display function. The associated query display function is a function capable of tracking and accessing a query cause item, and may provide page information including a query cause item and a link for moving to a page address including the query cause item. For example, although the query output unit 133 may provide a link for moving to a page address including the query cause item in the form of a user interface (UI), it is not limited thereto. Here, the page information may include the title of the page including the query cause item. In addition, although the page information may include the number of visits of the test subject, the classification title of the clinical trial data, and the like, it is not limited thereto.

For example, the query output unit 133 may output a message corresponding to a query generation condition, and provide a first button UI for providing an associated query display function on one side of the message.

When the first button UI is clicked on the user terminal 400, the query output unit 133 may provide the associated query display function on one side of the first button UI. The query output unit 133 may provide the associated query display function as page information including the query cause item and a second button UI including the query cause item name. In addition, when the second button UI is clicked, the query output unit 133 may provide a link function for moving to a page address including the query cause item.

Furthermore, when the query generation condition of the query target item is set based on a relationship with a plurality of items, the query output unit 133 may provide page information including a query cause item and a link for moving to a page address including the query cause item for each of the plurality of query cause items.

For example, when a query generation condition of a query target item is set based on a relationship with a plurality of items, and the query generation determination unit 132 determines that data input by the user terminal 400 corresponds to each query generation condition in the relationship with a plurality of items, the query output unit 133 may provide page information including a plurality of query cause items and links for moving to a page address including the query cause item on one side of the first button UI, respectively.

As another example, although a query generation condition of a query target item is set based on a relationship with a plurality of items, and the query generation determination unit 132 determines that data input by the user terminal 400 corresponds to a query generation condition in the relationship with any one item among the plurality of items, the query output unit 133 may provide page information including a plurality of query cause items and links for moving to a page address including the query cause item on one side of the first button UI, respectively.

The query output unit 133 may provide a cause item display function for highlighting the query cause item on the moved page. Although the highlight display of the query cause item may disappear after being maintained for a predetermined time period, it is not limited thereto. For example, the highlight display of the query cause item may be continuously maintained, or it may be implemented to disappear by input of the user terminal 400. The predetermined time period may be a time period set by the manager terminal 300 or the system.

In addition, the query output unit 133 may provide a function of directly moving from a page including a query cause item to a page including a query target item. For example, the query output unit 133 may provide a function of moving to a page including a query target item by providing a pop-up window to the user terminal 400 when the highlight display disappears by input of the user terminal 400 on a page including the query cause item. However, it is not limited thereto, and the function of directly moving to a page including a query target item may be provided in various methods.

Accordingly, the user terminal 400 may easily confirm, in inputting clinical trial data, a query cause item on a page including query target items, and move to a page address including the query cause item. Therefore, it may be advantageous for the user terminal 400 to reduce the time and cost required for confirming a query generation cause and correcting or verifying data.

Hereinafter, a process of the query output unit 133 for providing a function of outputting a query and displaying an associated query according to an embodiment will be described in more with reference to FIGS. 4 to 6 using a specific example of generating a query according to selection of an item of 'Confirmed positive pregnancy test result—' among the clinical trial withdrawn items input from the user terminal 400.

Figure 4:
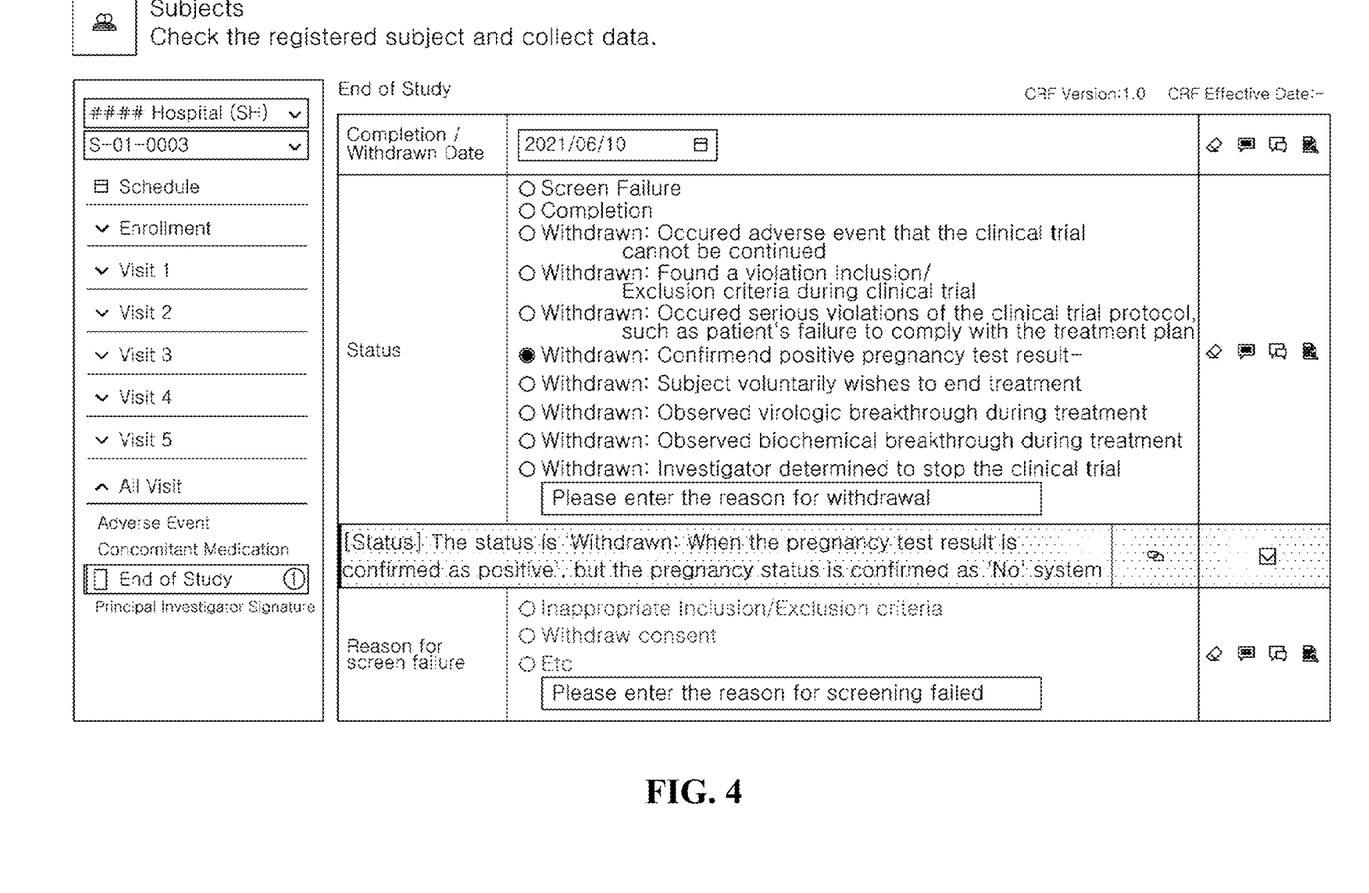
FIG. 4 is a view showing an example of a screen on which a query is output in a page including a query target item.

FIG. 4 is a view showing an example of a screen on which a query is output in a page including a query target item. FIG. 5 is an enlarged view showing an example of a screen on which an associated query display function is provided on the page of FIG. 4. FIG. 6 is a view showing an example of a screen on which a user terminal moves from the page of FIG. 5 to a page including a query cause item through an associated query display function.

When 'No' is selected for the pregnancy state item as previous input data although the user terminal 400 selects the 'Confirmed positive pregnancy test result—' among the clinical trial withdrawn items, the query generation determination unit 132 may request the query output unit 133 to output a query, and store the pregnancy state item in the query item storage unit 134.

In this case, as shown in FIG. 4, the query output unit 133 may output a previously stored message (the state is 'Withdrawn: When the pregnancy test result is confirmed as positive', but the pregnancy status is confirmed as 'No') as a query on the page including the clinical trial withdrawn items. In FIG. 4, although the query is output under the query target items as an example, it is not limited thereto, and it may be variously modified to output the query on one side of the query target item or to output in the form of a pop-up window on the current page of the user terminal 400.

Figure 5:
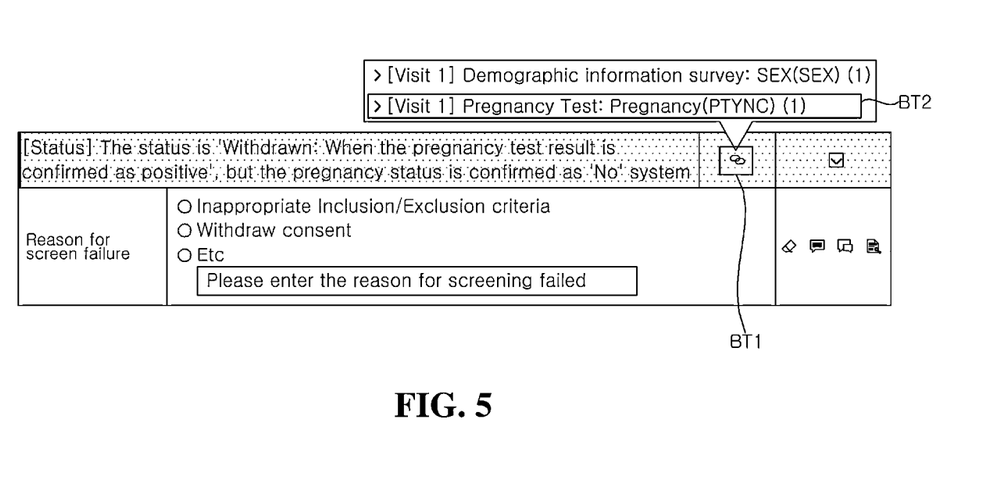
FIG. 5 is an enlarged view showing an example of a screen on which an associated query display function is provided on the page of FIG. 4.

In addition, as shown in FIG. 5, the query output unit 133 may provide a first button UI BT1 for providing an associated query display function on one side of the message. When the first button UI BT1 is clicked on the user terminal 400, the query output unit 133 may provide page information including the query cause item and the second button UI BT2 including the query cause item name.

It is shown in FIG. 5 as an example that as the query generation condition of 'Confirmed positive pregnancy test result—' among the clinical trial withdrawn items is set based on a relationship with the item for sex and the item for pregnancy, the query output unit 133 provides a link, which includes the page information and the item name of each of the items for sex and pregnancy state, for moving to each page. However, in another embodiment, only a link including the page information and the item name of the pregnancy state item, which is a query generation cause, may be provided.

Figure 6:
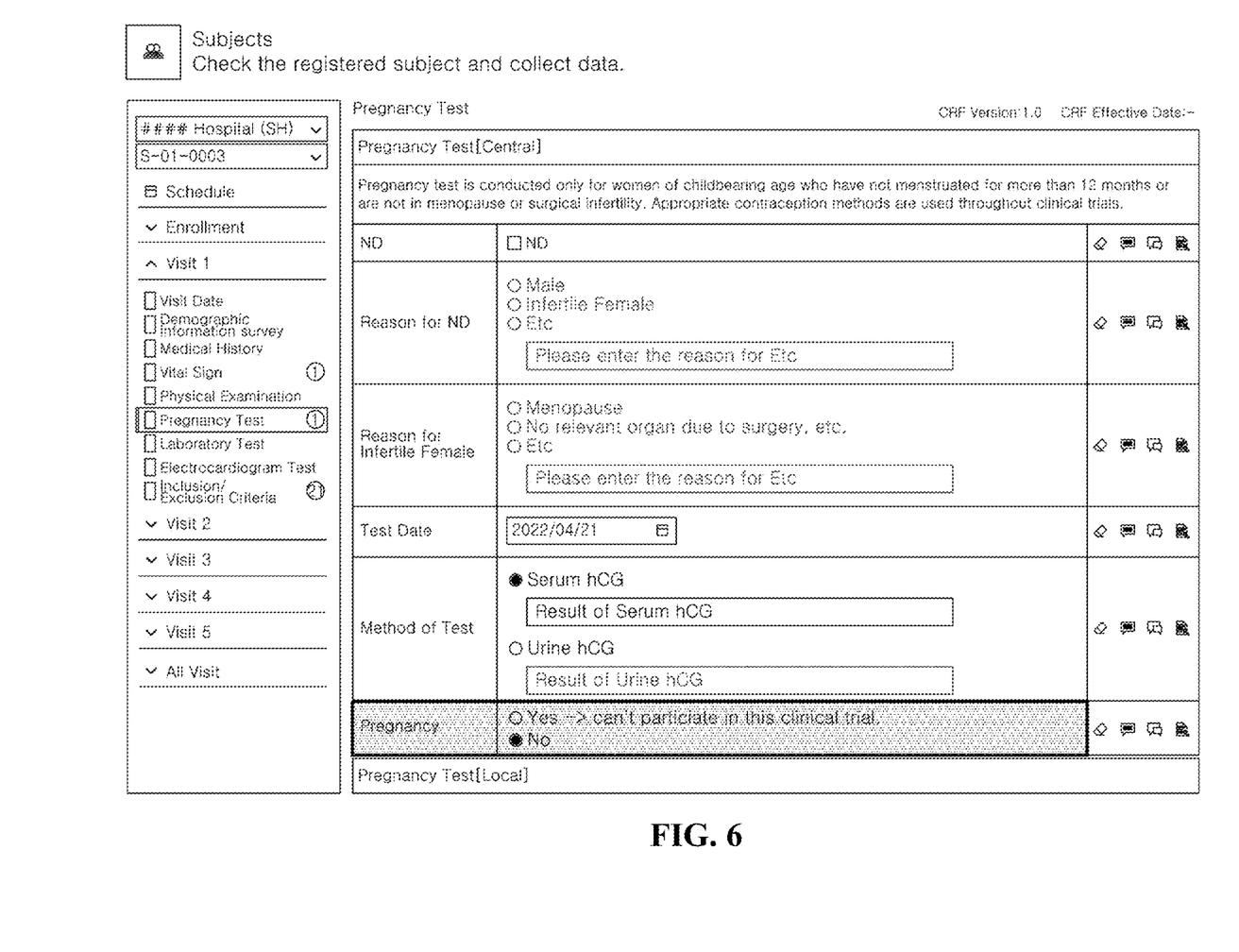
FIG. 6 is a view showing an example of a screen on which a user terminal moves from the page of FIG. 5 to a page including a query cause item through an associated query display function.

Then, when the second button UI2 is clicked on the user terminal 400, it may move to a pregnancy test page including a pregnancy state item, and the query output unit 133 may highlight the pregnancy state item as shown in FIG. 6. The highlight display may disappear after being maintained for a predetermined time period after moving to the page, or disappear when there is an input from the user terminal 400.

In addition, although it is not shown in detail, the query output unit 133 may provide a function of moving to a page including a query target item to the user terminal 400 when the highlight display disappears. That is, the query output unit 133 may provide a pop-up window for moving to a clinical trial end page including the query target item to the user terminal 400 when the highlight display of the pregnancy state item disappears from the pregnancy test page.

As described above, as the query output unit 133 according to an embodiment provides a function of displaying an associated query and a function of moving from a page including a query cause item to a page including a query target item, it may be advantageous for the user terminal 400 to reduce the time and cost required for confirming a query generation cause and correcting or verifying data.

The query item storage unit 134 may store a query cause item related to a query generated when the user terminal 400 inputs clinical trial data on the electronic case report form. In addition, in some embodiments, the query item storage unit 134 may store a query generation time and date, page movement information of the user terminal 400 when a query is generated, whether clinical trial data is corrected by the user terminal 400, and the like (hereinafter, referred to as query generation related information).

The query item storage unit 134 may store a query cause item in correspondence to electronic case report form related information, such as manager information and/or user information, and generate a query cause item list. In some embodiments, the query cause item list may include query generation related information, such as a query generation time and date, page movement information of the user terminal 400 when a query is generated, and whether clinical trial data is corrected by the user terminal 400.

The query item storage unit 134 may provide a query cause item list corresponding to manager information and/or user information in response to a request of the manager terminal 300 and/or the user terminal 400.

Accordingly, the manager terminal 300 and the user terminal 400 may easily input or manage clinical trial data and queries therefor, and increase reliability of the clinical trial data by securing consistency of the clinical trial data.

Referring to FIG. 2 again, the data storage unit 140 may store data exchanged with the manager terminal 300, the user terminal 400, and other platforms. The data storage unit 140 according to an embodiment may include a manager DB 141, a user DB 142, a case report form DB 143, a query DB 144, and a clinical data DB 145.

The manager DB 141 may store manager information such as the manager's email, ID, password, phone number, affiliated group information, and the like, and information on access of the manager terminal 300 to the platform 100.

The user DB 142 may store user information such as the user's email, ID, password, phone number, affiliated group information, and the like, and information on access of the user terminal 400 to the platform 100.

The case report form DB 143 may store the electronic case report form and the electronic case report form related information. When the electronic case report form and the electronic case report form related information are stored, the case report form DB 143 may classify and store them according to the electronic case report form related information. For example, the case report form DB 143 may classify and store them by generating a directory corresponding to any one among the clinical trial title, protocol number, manager information, and user information of the electronic case report form.

The query DB 144 may receive and store a query generation condition and a message to be output when a query is generated, from the query condition setting unit 131. The query DB 144 may store a query generation condition and a message to be output when a query is generated in correspondence to the electronic case report form related information. In addition, the query DB 144 may store a message to be output when a query is generated in correspondence to each query generation condition.

The clinical data DB 145 may store clinical trial data input from the user terminal 400. The clinical data DB 145 may store clinical trial data in correspondence to electronic case report form related information. In some embodiments, the clinical data DB 145 may store query cause items and query generation related information stored in the query item storage unit 134, together with clinical trial data input from the user terminal 400.

Figure 7:
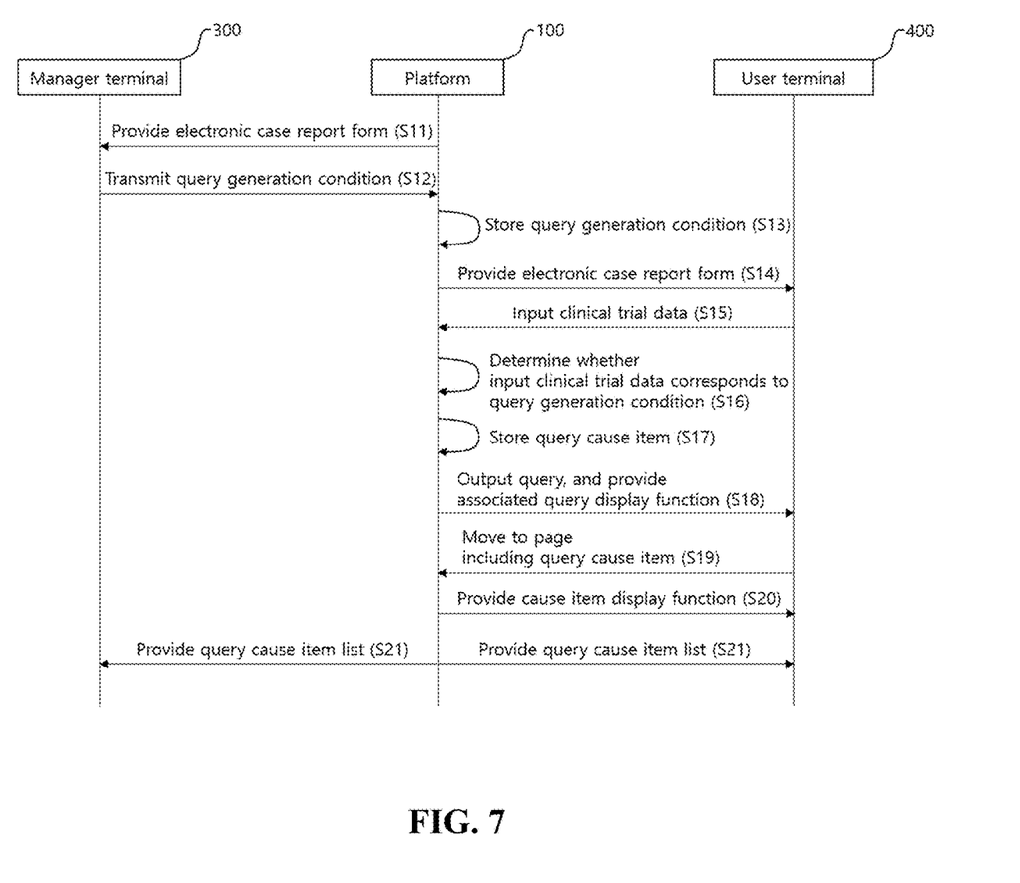
FIG. 7 is a flowchart illustrating an associated query display method of an associated query display system according to an embodiment.

FIG. 7 is a flowchart illustrating an associated query display method of an associated query display system according to an embodiment.

Referring to FIGS. 1 to 3 and 7, the server management unit 110 may provide an electronic case report form to the manager terminal 300 in response to a request of the manager terminal 300 (S11).

The server management unit 110 may provide an electronic case report form to the manager terminal 300 through any one among an application program, an application, and a website. The electronic case report form may be stored in the case report form DB 143, together with electronic case report form related information including manager information before receiving a request from the manager terminal 300. Accordingly, the server management unit 110 may provide the electronic case report form corresponding to the manager information of the manager terminal 300 to the manager terminal 300.

The manager terminal 300 may transmit a query generation condition to the platform 100 (S12).

Although the query generation condition may be set in correspondence to each electronic case report form, it is not limited thereto. For example, the query generation condition may be commonly set for a plurality of electronic case report forms. In addition, the manager terminal 300 may transmit a message to be output when a query is generated to the platform 100. Here, the query generation condition may be substantially the same as the query generation condition described with reference to FIG. 3. Accordingly, a detailed description of the query generation condition will be omitted.

Although the query condition setting unit 131 may request electronic case report form related information of an electronic case report form, for which a query condition is to be set, in order to receive a query generation condition from the manager terminal 300, it is not limited thereto.

Although FIG. 7 shows an example of providing an electronic case report form so that the platform 100 may receive a query generation condition from the manager terminal 300, in another embodiment, the platform 100 may receive an electronic case report form and a query generation condition together from the manager terminal 300.

The query condition setting unit 131 may store the query generation condition and a message to be output when a query is generated, which are received from the manager terminal 300, in the query DB 144 (S13).

The query DB 144 may store a query generation condition and a message to be output when a query is generated in correspondence to the electronic case report form related information. In addition, the query DB 144 may store a message to be output when a query is generated in correspondence to each query generation condition.

Then, the server management unit 110 may provide the electronic case report form in response to a request of the user terminal 400.

The server management unit 110 may provide the electronic case report form to the user terminal 400 through any one among an application program, an application, and a website. Although the server management unit 110 may request user information in order to provide an electronic case report form to the user terminal 400, and provide the electronic case report form corresponding to the user information, it is not limited thereto.

When clinical trial data is input from the user terminal 400 (S15), the query generation determination unit 132 may determine whether the clinical trial data input from the user terminal 400 corresponds to a query generation condition (S16).

When data is input for each item of the electronic case report form from the user terminal 400, the query generation determination unit 132 may confirm the query generation condition set for each item, and determine whether the data input from the user terminal 400 corresponds to a query generation condition.

When the data input from the user terminal 400 corresponds to a query generation condition, the query generation determination unit 132 may request the query output unit 133 to output a query, and store an item that causes the query (or a query cause item) in the query item storage unit 134 (S17).

The query item storage unit 134 may store a query cause item in correspondence to electronic case report form related information, such as manager information and/or user information. In addition, in some embodiments, when the query cause item is stored, the query item storage unit 134 may store corresponding query generation time and date together.

The query output unit 133 may output the query on the user terminal 400 in response to a request of the query generation determiner 132, and provide an associated query display function (S18).

The query output unit 133 may output a message, which is stored in the query DB 144 in correspondence to a query generation condition and to be output when a query is generated, as a query. The query output unit 133 may output the query on the user terminal 400 through any one among an application program, an application, and a website. In this case, the query output unit 133 may output the query on the page where the query target item is displayed.

The associated query display function is a function of tracking and accessing a query cause item, and may include page information including a query cause item and a link for moving to a page address including the query cause item. Here, the page information may include the title of the page including the query cause item. In addition, although the page information may include the number of visits of the test subject, the classification title of the clinical trial data, and the like, it is not limited thereto.

For example, the query output unit 133 may output a message corresponding to a query generation condition, and provide a first button UI for providing an associated query display function on one side of the message.

When the first button UI is clicked on the user terminal 400, the query output unit 133 may provide the associated query display function on one side of the first button UI. The query output unit 133 may provide the associated query display function as page information including the query cause item and a second button UI including the query cause item name. In addition, when the second button UI is clicked, the query output unit 133 may provide a link function for moving to a page address including the query cause item.

Furthermore, when the query generation condition of the query target item is set based on a relationship with a plurality of items, the query output unit 133 may provide page information including a query cause item and a link for moving to a page address including the query cause item for each of the plurality of query cause items.

For example, when a query generation condition of a query target item is set based on a relationship with a plurality of items, and the query generation determination unit 132 determines that data input by the user terminal 400 corresponds to each query generation condition in the relationship with a plurality of items, the query output unit 133 may provide page information including a plurality of query cause items and links for moving to a page address including the query cause item on one side of the first button UI, respectively.

As another example, although a query generation condition of a query target item is set based on a relationship with a plurality of items, and the query generation determination unit 132 determines that data input by the user terminal 400 corresponds to a query generation condition in the relationship with any one item among the plurality of items, the query output unit 133 may provide page information including a plurality of query cause items and links for moving to a page address including the query cause item on one side of the first button UI, respectively.

The user terminal 400 may move to a page including a query cause item through the associated query display function (S19). In this case, the query output unit 133 may provide a cause item display function for highlighting the query cause item on the moved page (S20).

Although the highlight display of the query cause item may disappear after being maintained for a predetermined time period, it is not limited thereto. For example, the highlight display of the query cause item may be continuously maintained, or it may be implemented to disappear by input of the user terminal 400. The predetermined time period may be a time period set by the manager terminal 300 or the system.

Furthermore, although not specifically shown in FIG. 7, the query output unit 133 may provide a function of directly moving from a page including a query cause item to a page including a query target item. For example, the query output unit 133 may provide a function of moving to a page including a query target item by providing a pop-up window to the user terminal 400 when the highlight display disappears by input of the user terminal 400 on a page including the query cause item. However, it is not limited thereto, and the function of directly moving to a page including a query target item may be provided in various methods.

Then, the query item storage unit 134 may generate a query cause item list, and provide the query cause item list in response to a request of the manager terminal 300 and/or the user terminal 400 (S21).

The query item storage unit 134 may generate a query cause item list in correspondence to electronic case report form related information, such as manager information and/or user information. In some embodiments, the query cause item list may include query generation related information, such as a query generation time and date, page movement information of the user terminal 400 when a query is generated, and whether clinical trial data is corrected by the user terminal 400. However, it is not limited thereto.

The query item storage unit 134 may provide a query cause item list corresponding to manager information and/or user information in response to a request of the manager terminal 300 and/or the user terminal 400.

As described above, according to an associated query display method of an associated query display system according to an embodiment, the manager terminal 300 may easily manage queries generated when clinical trial data is collected, and may be advantageous in reducing the time and cost required in a communication process related to query generation with the user terminal 400. In addition, as the user terminal 400 may easily confirm, in inputting clinical trial data, a query cause item on a page including query target items, and move to a page address including the query cause item, it may be advantageous for the user terminal 400 to reduce the time and cost required for confirming a query generation cause and correcting or verifying data.

Furthermore, highly reliable clinical trial data can be collected by securing consistency of the clinical trial data input from the user terminal 400.

Until now, the present invention has been described in detail focusing on the embodiments shown in the drawings. These embodiments are intended to illustrate, rather than limit, the present invention, and should be considered in an illustrative viewpoint, rather than a restrictive viewpoint. The true technical protection scope of the present invention should be determined by the technical spirit of the appended claims rather than the above description. Although specific terms are used in this specification, they are used only for the purpose of describing the concept of the present invention, and are not used to limit the meaning or the scope of the present invention described in the claims. Each step of the present invention does not necessarily have to be performed in the described order, and may be performed in parallel, selectively, or individually. Those skilled in the art will understand that various modifications and equivalent other embodiments are possible without departing from the essential technical spirit of the present invention as claimed in the claims. It is to be understood that equivalents include both presently known equivalents, as well as equivalents that will be developed in the future, i.e., all components invented to perform the same function, regardless of the structure.

According to an associated query display system and a method thereof according to the embodiments, it may be advantageous in reducing the time and cost required for managing clinical trial data since it is easy to manage a query generated when clinical trial data is collected.

In addition, it is advantageous in reducing the time and cost required for confirming a query generation cause and correcting or confirming clinical trial data, and highly reliable clinical trial data may be collected by securing consistency of the clinical trial data.

The effects according to the embodiments of the present invention are not limited by the contents exemplified above, and more various effects are included in this specification.

DESCRIPTION OF SYMBOLS

10: Associated query display system
100: Platform
110: Server management unit
120: Server communication unit
130: Query management unit
140: Data storage unit
131: Query condition setting unit
132: Query generation determination unit
133: Query output unit
134: Query item storage unit

What is claimed is:

1. An associated query display method comprising the steps of:
   storing a query generation condition received from a manager terminal;
   receiving clinical trial data from a user terminal;
   determining whether the clinical trial data corresponds to the query generation condition;
   storing a query cause item that causes generation of a query; and
   displaying, on a display screen of the user terminal, the query including an associated query display function capable of tracking and accessing the query cause item,
   wherein the query generation condition is set as a logic error of the clinical trial data based on a relationship between a plurality of items,
   wherein the query cause item is at least one item of the plurality of items from which the logic error of the clinical trial data is set for the query generation condition, and
   wherein the associated query display function includes page information including the query cause item and a link for moving to a page address including the query cause item.

2. The method according to claim 1, wherein the step of storing a query generation condition received from a manager terminal includes the step of receiving and storing the query generation condition and a message to be output in correspondence to the query generation condition from the manager terminal.

3. The method according to claim 1, further comprising the step of providing, when the user terminal moves to a page including the query cause item through the associated query display function, a cause item display function for highlighting the query cause item on the moved page.

4. The method according to claim 3, further comprising the step of providing a function of directly moving from the moved page to a page including a query target item, which is a target of query generation.

5. The method according to claim 1, further comprising the step of providing a query cause item list to the manager terminal and/or the user terminal.

6. The method according to claim 5, wherein the query cause item list includes the query cause item stored at the step of storing a query cause item that causes generation of a query, and query generation related information including a time and date when the query is generated.

7. An associated query display system comprising one or more processors configured to:
   receive a query generation condition from a manager terminal;
   determine whether clinical trial data input from a user terminal corresponds to the received query generation condition;
   store, in a database, a query cause item that causes generation of a query; and
   display, on a display screen of the user terminal, the query including an associated query display function capable of tracking and accessing the query cause item,
   wherein the query generation condition is set as a logic error of the clinical trial data based on a relationship between a plurality of items,
   wherein the query cause item is at least one item of the plurality of items from which the logic error of the clinical trial data is set for the query generation condition, and
   wherein the associated query display function includes page information including the query cause item and a link for moving to a page address including the query cause item.

8. The system according to claim 7, wherein the one or more processors are further configured to provide, when the user terminal moves to a page including the query cause item through the associated query display function, a cause item display function for highlighting the query cause item on the moved page.

9. The system according to claim 8, wherein the one or more processors are further configured to provide a function of directly moving from the moved page to a page including a query target item, which is a target of query generation.

10. The system according to claim 7, wherein the one or more processors are further configured to provide a query cause item list including the query cause item and query generation related information including a time and date when the query is generated.

11. A non-transitory computer-readable storage medium containing instructions which when executed on a processor performs an associated query display method, the method comprising the steps of:
   storing a query generation condition received from a manager terminal;
   receiving clinical trial data from a user terminal;
   determining whether the clinical trial data corresponds to the query generation condition;
   storing a query cause item that causes generation of a query; and
   displaying, on a display screen of the user terminal, the query including an associated query display function capable of tracking and accessing the query cause item,
   wherein the query generation condition is set as a logic error of the clinical trial data based on a relationship between a plurality of items,
   wherein the query cause item is at least one item of the plurality of items from which the logic error of the clinical trial data is set for the query generation condition, and
   wherein the associated query display function includes page information including the query cause item and a link for moving to a page address including the query cause item.

\* \* \* \* \*